US00PP28058P2

(12) United States Plant Patent
Wezelenburg, Jr.

(10) Patent No.: US PP28,058 P2
(45) Date of Patent: May 30, 2017

(54) ***CERCIDIPHYLLUM* PLANT NAMED 'JWW4'**

(50) Latin Name: *Cercidiphyllum japonicum*
Varietal Denomination: JWW4

(71) Applicant: Jan-Willem Wezelenburg, Jr., Hazerswoude-Dorp (NL)

(72) Inventor: Jan-Willem Wezelenburg, Jr., Hazerswoude-Dorp (NL)

(73) Assignee: JAN-WILLEM WEZELENBURG BOSKOOP B.V., Hazerswoude-Dorp (NL)

( * ) Notice: Subject to any disclaimer, the term of this patent is extended or adjusted under 35 U.S.C. 154(b) by 38 days.

(21) Appl. No.: 14/756,736

(22) Filed: Oct. 6, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

UPOV—Plant Variety Database, Jan. 4, 2017, citation for 'JWW4' (1 page).*

* cited by examiner

*Primary Examiner* — Susan McCormick Ewoldt
(74) *Attorney, Agent, or Firm* — Penny J. Aguirre

(57) ABSTRACT

A new cultivar of *Cercidiphyllum japonicum* plant named, 'JWW4', that is characterized by its compact, upright, even, and nearly globular plant habit, its growth habit that does not form a central leader, and its young shoots that are bronze-orange in color.

2 Drawing Sheets

Botanical classification: *Cercidiphyllum japonicum.*
Variety denomination: 'JWW4'.

BACKGROUND OF THE INVENTION

The present invention relates to a new and distinct cultivar of *Cercidiphyllum japonicum* and will be referred to hereafter by its cultivar name, 'JWW4'. 'JWW4' is a new cultivar of Katsura tree for use as an ornamental landscape plant.

The Inventor selected the new cultivar, 'JWW4', as a seedling in a seedbed at his nursery in Hazerswoude-Dorp, The Netherlands in June of 2008. The seedbed had been planted with seeds collected from an unnamed and unpatented proprietary seedling of *Cercidiphyllum japonicum* that had been open pollinated.

Asexual propagation of the new cultivar was first accomplished by the Inventor by grafting in summer of 2009 in Hazerswoude-Dorp, The Netherlands. Asexual propagation by grafting has determined that the unique characteristics of the new cultivar are stable and reproduced true to type in successive generations.

SUMMARY OF THE INVENTION

The following traits have been repeatedly observed and represent the characteristics of the new cultivar. These attributes in combination distinguish 'JWW4' as a unique cultivar of *Cercidiphyllum.*

1. 'JWW4' exhibits a compact, upright, even, nearly globular plant habit.
2. 'JWW4' exhibits a growth habit that does not form a central leader.

3. 'JWW4' exhibits young shoots that are bronze-orange in color.

The female plant differs from 'JWW4' in having a short central leader, in having a less compact plant habit and in lacking young shoots that are bronze-orange in color. 'JWW4' can be most closely compared to the *Cercidiphyllum japonicum* cultivars 'Heronswood Globe' (not patented) and 'Krukenberg Dwarf' (not patented). Both are similar to 'JWW4' in having a compact plant habit. Both 'Heronswood Globe' and 'Krukenberg Dwarf' differ from 'JWW4' in having a short central leader, in having an ovate plant shape, and in having young shoots that are reddish purple in color.

BRIEF DESCRIPTION OF THE DRAWINGS

The accompanying colored photographs illustrate the overall appearance and distinct characteristics of the new *Cercidiphyllum.* The photographs were taken of a two year-old plant of the new cultivar as grown outdoors in 21-cm containers in Hazerswoude-Dorp, The Netherlands.

The photograph in FIG. 1 provides a side view of the overall plant habit of 'JWW4'.

Figure 1:
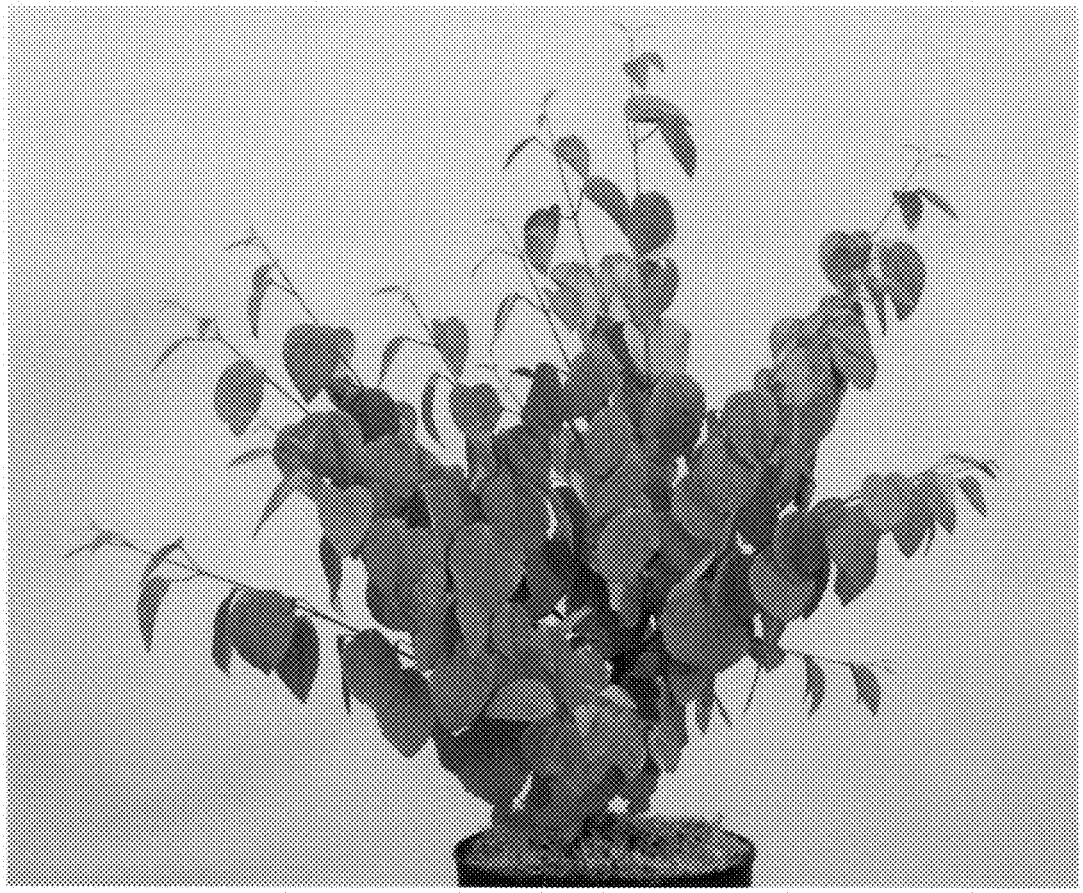
Figure 2:
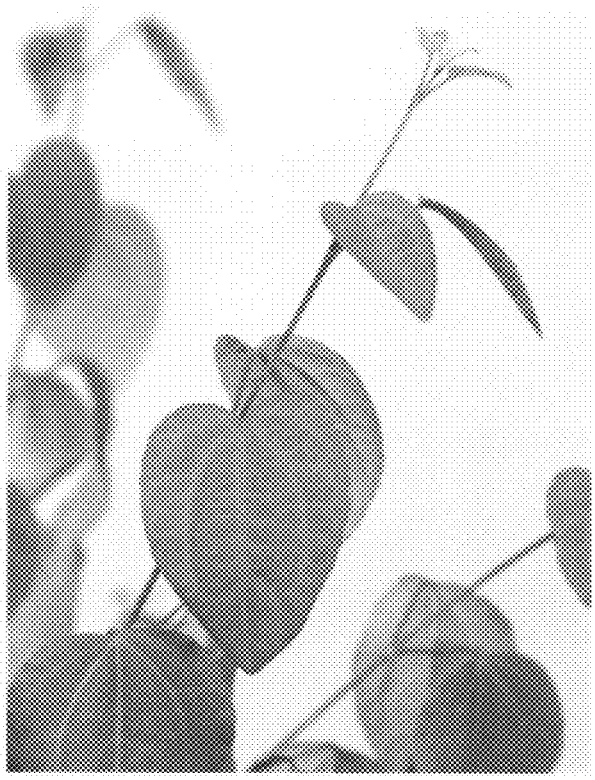

The photograph in FIG. 2 provides a close up view of the young shoots of 'JWW4'.

Figure 3:
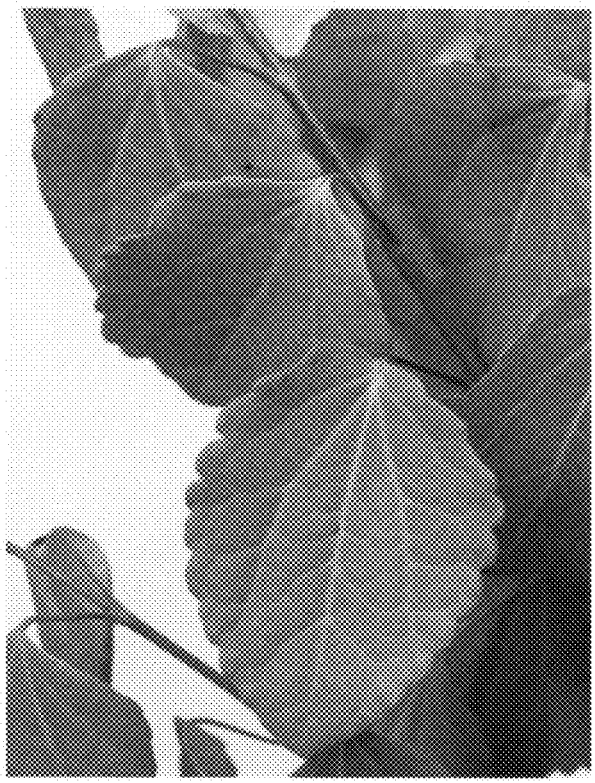

The photograph in FIG. 3 provides a close-up view of the mature foliage and stems of 'JWW4'.

The colors in the photographs are as close as possible with the photographic and printing technology utilized and the color values cited in the detailed botanical description accurately describe the colors of the new *Cercidiphyllum.*

DETAILED BOTANICAL DESCRIPTION

The following is a detailed description of two year-old plants of the new cultivar as grown outdoors in 21-cm containers in Hazerswoude-Dorp, The Netherlands. Plants were grown under average day temperatures ranging from 12° to 25° C. and average night temperatures of 4° to 15° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Flowering have not been observed on the new cultivar.

*Plant type.*—Deciduous shrub.

*Plant habit.*—Compact, upright, globular to broadly ovate shape.

*Plant size.*—Reaches an average of 3.5 m in height and spread as a ten year-old plant in the landscape.

*Cold hardiness.*—At least in U.S.D.A. Zone 5.

*Diseases and pests.*—Similar to other *Cercidiphyllum japonicum* cultivars, which typically are disease and pest free.

*Root description.*—Fibrous and fine.

*Growth rate.*—Moderate, 24 months to fully develop in a 21-cm container.

Branch description:

*Branch shape.*—Round.

*Branch color.*—Young shoots; upper surface emerges a blend of 180A and 181A and changes to 164A, lower surface 146D, mature branches on upper and lower surfaces; a blend between 148B and 197B, bark (mature branches and trunk); 199A and 199B and 200A.

*Branch size.*—An average of 26.1 cm in length and 2 mm in diameter.

*Trunk diameter.*—2.5 cm measured 2 cm above the soil line on a 2 year-old tree.

*Branch surface.*—Glabrous and glossy, bark smooth, glabrous and slightly glossy.

*Branch aspect.*—Held at an average angle of 30° to main stem, other lateral branches held at an average angle of 55° to main stem.

*Branch strength.*—Very strong.

*Branching.*—Free branching, an average of 18 lateral branches.

*Internode length.*—An average of 3.6 cm.

Foliage description:

*Leaf shape.*—Broadly ovate to obovate to nearly orbicular.

*Leaf division.*—Simple.

*Leaf base.*—Obtuse to undeeply truncate or very short acuminate.

*Leaf apex.*—Obtuse to broadly acute.

*Leaf fragrance.*—A pleasant "burnt sugar" like fragrance, typical for *Cercidiphyllum* present in autumn when leaves have dropped.

*Leaf venation.*—Laciniate, color; upper surface 144B to 144C and lower surface 144C to 144D.

*Leaf margins.*—Crenate.

*Leaf arrangement.*—Opposite.

*Leaf attachment.*—Petiolate.

*Leaf surface.*—Glabrous, both sides matte.

*Leaf size.*—An average of 7.2 cm in length and 6.4 cm in width.

*Leaf quantity.*—An average of 16 (8 pairs).

*Leaf color.*—Young upper surface; a blend of 174A and 180A, young lower surface; 147C and suffused with 176C, mature upper surface; 143A to 143B, mature lower surface; 138B, fall color; primarily 12A and 13B on both surfaces, fading to 28B and darker (strongly depending on local climatological and environmental circumstances).

*Petioles.*—An average of 3.2 mm in length and 1.5 mm in width, color; upper surface 180B and lower surface 153D with 145D at proximal and distal ends, smooth surface.

*Stipules.*—A small filiform is present on the upper side of the base of the petiole, 3 mm in length and 0.5 mm in width, cuneate base, narrow acute to cleft apex, 150D in color.

Inflorescence/fruit description: No flowers or fruit have been observed to date.

It is claimed:

1. A new and distinct cultivar of *Cercidiphyllum* plant named 'JWW4' as herein illustrated and described.

* * * * *